US011717344B2

(12) United States Patent
Valls et al.

(10) Patent No.: US 11,717,344 B2
(45) Date of Patent: Aug. 8, 2023

(54) MEDICAL PROBE WITH WIRING DISPOSED BETWEEN TWO EXPANDABLE MEMBRANES

(71) Applicant: Biosense Webster (Israel) Ltd., Yokneam (IL)

(72) Inventors: Jace P. Valls, Pasadena, CA (US); Diana S. Gallardo, Wildomar, CA (US); Charles E. Perkins, Danvers, MA (US); Don Q. Ngo-Chu, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 359 days.

(21) Appl. No.: 16/657,319

(22) Filed: Oct. 18, 2019

(65) Prior Publication Data

US 2020/0155226 A1 May 21, 2020

Related U.S. Application Data

(60) Provisional application No. 62/769,424, filed on Nov. 19, 2018.

(51) Int. Cl.
*A61B 18/14* (2006.01)
*A61B 18/00* (2006.01)
*A61B 90/00* (2016.01)
*A61M 25/10* (2013.01)

(52) U.S. Cl.
CPC ...... *A61B 18/1492* (2013.01); *A61B 18/1485* (2013.01); *A61B 2018/0022* (2013.01); *A61B 2018/00577* (2013.01); *A61B 2018/00791* (2013.01); *A61B 2018/1405* (2013.01);

(Continued)

(58) Field of Classification Search
CPC ........ A61B 1/00082; A61B 2018/0016; A61B 2018/00214; A61B 2018/0022; A61B 2018/00238; A61B 2018/00285; A61B 2018/00577; A61B 2218/002; A61B 2562/164; A61B 5/6853; A61M 25/10–2025/1097
See application file for complete search history.

(56) References Cited

U.S. PATENT DOCUMENTS

| 4,709,698 A | * | 12/1987 | Johnston | ................ A61B 18/08 606/41 |
| 2002/0198521 A1 | * | 12/2002 | Maguire | .................. A61N 7/02 606/41 |

(Continued)

FOREIGN PATENT DOCUMENTS

| WO | 2014/168987 A1 | 10/2014 | |
| WO | WO-2017087549 A1 | * 5/2017 | ......... A61B 1/00009 |

OTHER PUBLICATIONS

Extended European Search Report dated Apr. 2, 2020, from corresponding European Application No. 19209784.8.

*Primary Examiner* — Jaymi E Della
(74) *Attorney, Agent, or Firm* — Troutman Pepper Hamilton Sanders LLP (57) ABSTRACT

Shown and described is electrophysiology catheter end effector having a balloon with three expandable membranes attached to each other such that wiring (for the electrodes or other sensors on the membrane surfaces) no longer extend from inside the first membrane yet at the same time is captured between the first membrane and a second membrane.

17 Claims, 5 Drawing Sheets

(52) U.S. Cl.
CPC ................ *A61B 2090/3966* (2016.02); *A61M 2025/1043* (2013.01)

(56) References Cited

U.S. PATENT DOCUMENTS

| | | | | |
|---|---|---|---|---|
| 2008/0051707 A1* | 2/2008 | Phan | ................ | A61M 25/1006 604/108 |
| 2012/0071870 A1* | 3/2012 | Salahieh | ............ | A61B 1/00181 606/33 |
| 2013/0090649 A1* | 4/2013 | Smith | ................ | A61B 18/1492 606/41 |
| 2013/0274562 A1* | 10/2013 | Ghaffari | ............... | A61B 5/6833 601/3 |
| 2013/0274658 A1* | 10/2013 | Steinke | ............. | A61B 18/1492 606/41 |
| 2015/0112256 A1* | 4/2015 | Byrne | ............... | A61M 25/1029 604/103.02 |
| 2016/0374748 A9* | 12/2016 | Salahieh | ............ | A61B 18/1492 606/34 |
| 2017/0312022 A1 | 11/2017 | Beeckler et al. | | |
| 2017/0348049 A1* | 12/2017 | Vrba | ................. | A61B 18/1492 |

\* cited by examiner

MEDICAL PROBE WITH WIRING DISPOSED BETWEEN TWO EXPANDABLE MEMBRANES

CROSS-REFERENCE TO RELATED APPLICATIONS

This application claims the benefit of priority under 35 U.S.C. § 119 to prior filed U.S. Provisional Patent Application No. 62/769,424 filed on Nov. 19, 2018, the entire contents of which is incorporated herein by reference in its entirety as if fully set forth herein.

BACKGROUND

Ablation of cardiac tissue has been used to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters may be visualized using fluoroscopy.

SUMMARY OF THE DISCLOSURE

In the manufacturing of a medical probe having a balloon and electrodes arrayed on the balloon, we have determined that the electrical connection between a thermocouple (i.e., temperature sensor) on each electrode may not be optimal when the thermocouple/electrode is connected to wires that extends from inside the balloon due to the number of wires (referenced also as a "bifilar") connecting to the ten or more electrodes on the balloon. Accordingly, applicant has devised an electrophysiology catheter having a balloon with three expandable membranes attached to each other such that the wires no longer extend from inside the first membrane yet at the same time is captured between the first membrane and a second membrane.

Specifically, we have devised an electrophysiology probe that includes a tubular member, a first expandable membrane, a second expandable membrane, a plurality of electrodes with a plurality of wires connected to the electrodes. The tubular member extends along a longitudinal axis from a first end to a second end with a first expandable membrane having an outer surface and an inner surface disposed about the longitudinal axis. The first expandable membrane has a first expandable membrane portion being coupled to the second end of the tubular member and second expandable membrane portion spaced apart from the first expandable membrane portion along the longitudinal axis. The first expandable membrane is configured to be expanded from a compressed shape to a balloon shaped member. The plurality of electrodes are disposed on the outer surface of the first expandable membrane with one or more wires connected to each of the plurality of electrodes. Each wire extends from the tubular member to the electrode. The second expandable membrane encapsulates the one or more wires between the second expandable membrane and the first expandable membrane so that the wires are constrained between the first and second expandable membrane with the electrodes exposed to ambient environment.

The probe is also configured to have the following features, which can be combined into various combinations or permutations, such as, for example, the tubular member defines a first lumen that extend from the first end to the second end so that the wires are contained in the first lumen; the tubular member defines a second lumen that extends through the first expandable membrane to allow for another instrument to pass through the second lumen; the tubular member defines a third lumen that extends to a portion within the first expandable membrane, the third lumen configured to allow irrigation fluid to be delivered to the portion within the first expandable membrane; the first expandable membrane includes a plurality of openings that extends through the membrane to allow for irrigation fluid to flow from inside the membrane to outside of the membrane; the electrodes extend from a central electrode portion equiangularly about the longitudinal axis from the first expandable membrane portion towards the second expandable membrane portion such that the second expandable membrane encapsulates a portion of each of the electrodes proximate the second expandable membrane portion; wherein each of the plurality of electrodes defines a fishbone pattern not covered by the second expandable membrane; each electrode is coupled to the outer surface of the first expandable membrane via a substrate; a radiopaque marker is defined by a fish-head portion of each electrode; each electrode includes a radiopaque marker having a configuration different from other radiopaque markers on the other electrodes; a third expandable membrane disposed proximate the first expandable membrane portion so that the third expandable membrane encircles a portion of the first expandable membrane about the longitudinal axis; the third expandable membrane encapsulates a portion of a substrate for each of the plurality of electrodes between the first expandable membrane and the third expandable membrane; a retaining ring disposed about the third expandable membrane; the first expandable membrane includes a circumferential surface area of approximately 52% of a total surface area of the first expandable membrane that is not covered by the second and third expandable membranes; each substrate for each electrode includes a substrate surface area approximately 8 percent of the exposed outer circumferential surface area of the first expandable membrane; the plurality of electrodes comprises ten electrodes disposed equiangularly about the longitudinal axis on the first membrane; the second expandable membrane and third expandable membrane cover approximately half of the outer surface area of the first expandable membrane; the first expandable membrane includes a generally spheroidal member with a diameter as referenced to the longitudinal axis of about 30 millimeters and wherein the second expandable membrane and the third expandable membrane each includes a hemi-spherical member; or the first expandable membrane includes a first configuration disposed in a tubular member of less than 8 French and a second configuration disposed outside the tubular member of about 30 millimeters as referenced to the longitudinal axis.

BRIEF DESCRIPTION OF THE DRAWINGS

While the specification concludes with the claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Ablation of cardiac tissue to correct a malfunctioning heart is a well-known procedure for implementing such a correction. Typically, to successfully ablate, cardiac electro potentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation. The medical probe used in the ablation procedure are therefore known as an electrophysiology probe. Such probe may have a handle connected to a mapping and diagnostic system, which can be understood from commonly owned U.S. patent application Ser. No. 15/939,154 filed on Mar. 28, 2018 entitled IRRIGATED ELECTROPHYSIOLOGY CATHETER WITH DISTINGUISHABLE ELECTRODES FOR MULTI-ELECTRODE IDENTIFICATION AND ORIENTATION UNDER 2-D VISUALIZATION, which is hereby incorporated by reference with a copy attached to the Appendix.

Figure 1:
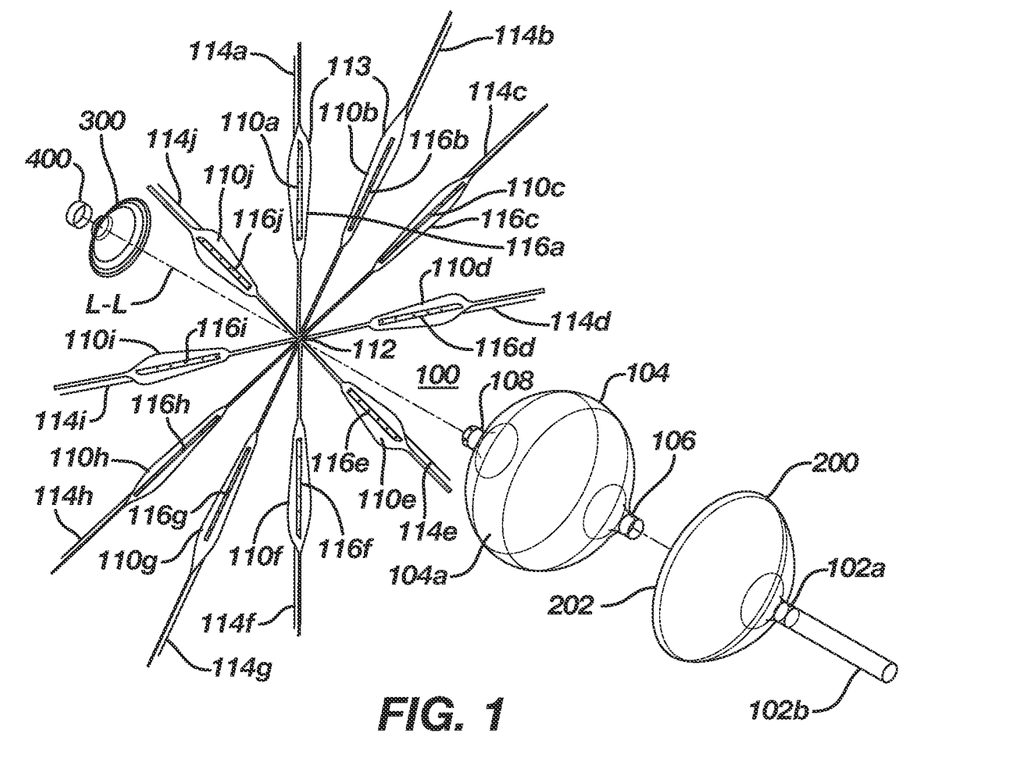
FIG. 1 is an exploded perspective view of the medical probe which shows a base balloon or first expandable membrane with radiating electrode assemblies that are partially covered by respective second and third expandable membranes.

FIG. 1 illustrates an exploded perspective view of an electrophysiology probe 100 that includes a tubular member 102 extending along a longitudinal axis L-L from a first (proximal) end 102b to a second (or distal) end 102a. A first expandable membrane 104 is attached to the tubular member 102 near the distal end 102b. The membrane 104 has an outer surface 104a and an inner surface 104b disposed about the longitudinal axis L-L. The outer surface 104a is exposed to the ambient environment while the inner surface 104b is exposed to the internal volume of the balloon defined by the membrane 104. The first expandable membrane 104 has a first expandable distal membrane portion 108 being coupled to the second end 102a of the tubular member 102 and second expandable distal membrane portion 106 spaced apart from the first expandable distal membrane portion 108 along the longitudinal axis L-L.

It is noted that first expandable membrane 104 is configured to be expanded from a compressed shape (generally tubular configuration) to a balloon (or generally spheroidal) shaped member. A plurality of electrodes (110a, 110b, 110c, 110d, 110e, 110f, 110g, 110h, 110i and 110j, which may be referred to singularly or collectively as "electrode 110") are disposed on the outer surface 104a of the first expandable membrane 104. The electrodes 110 are arranged so that they radiate from a generally common center or centroid substrate 112 near the second expandable distal membrane portion 108 which is distal to the tubular member 102. The electrodes 110a-110j may have one or more wires, i.e., bifilar 114a-114j, respectively, connected to each of the plurality of electrodes 110a-110j via a connection junction 116a-116j. Each of the wires 114a-114j (which may be singular in form "wire" or plural "wires" will be collectively referred to as "wire 114") is connected to the connection point at the "underside" surface of the electrode 110. The underside surface of each electrode 110 is the electrode surface that is not exposed to the ambient environment and is typically bonded to the outer surface 104a of the membrane 104. As the connection point 116 (typically a solder point) is generally at the center of the electrode, the wire is covered by the underside surface of each electrode. However, as each wire or bifilar 114a-114j extends toward the tubular member 102, the electrode surface or the substrate on which the electrode is bonded thereto becomes smaller thereby leaving the wire or bifilars 114a-114j exposed.

Figure 2:
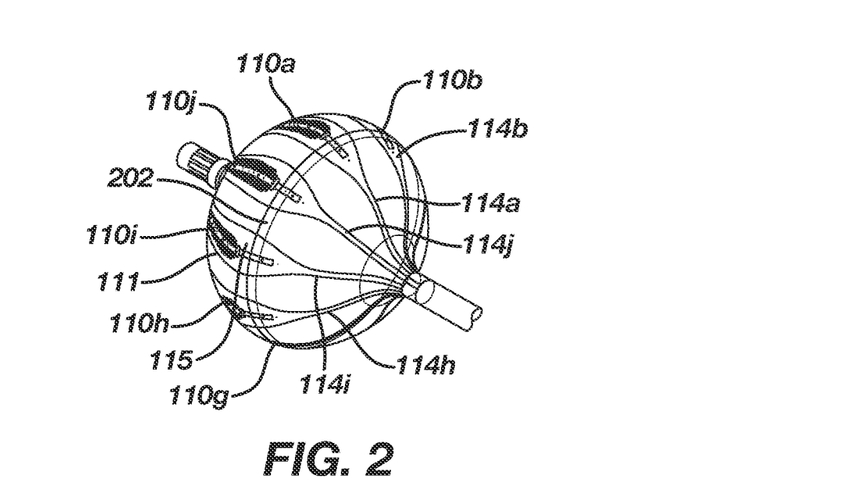
FIG. 2 illustrates an assembled medical probe of FIG. 1.
Figure 3A:
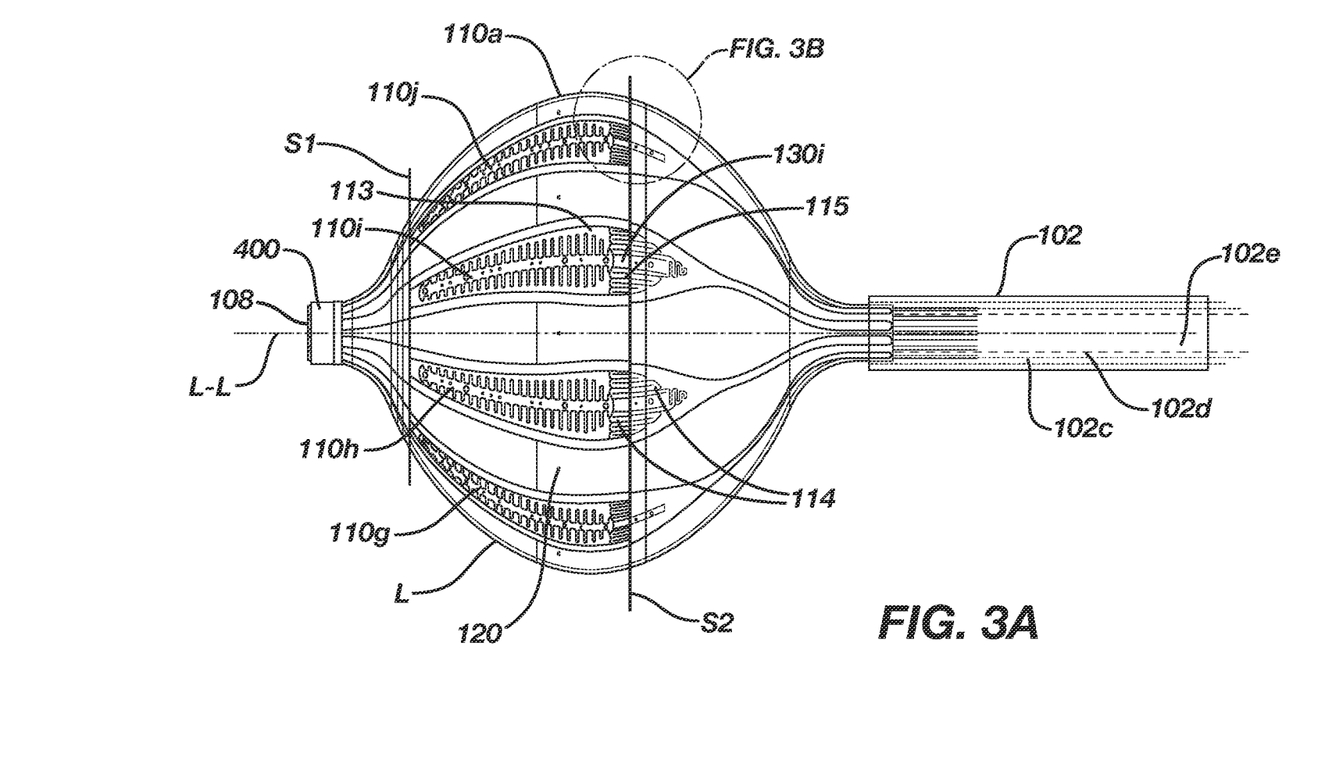
FIG. 3A is a side view of the medical probe of FIG. 2.
Figure 3B:
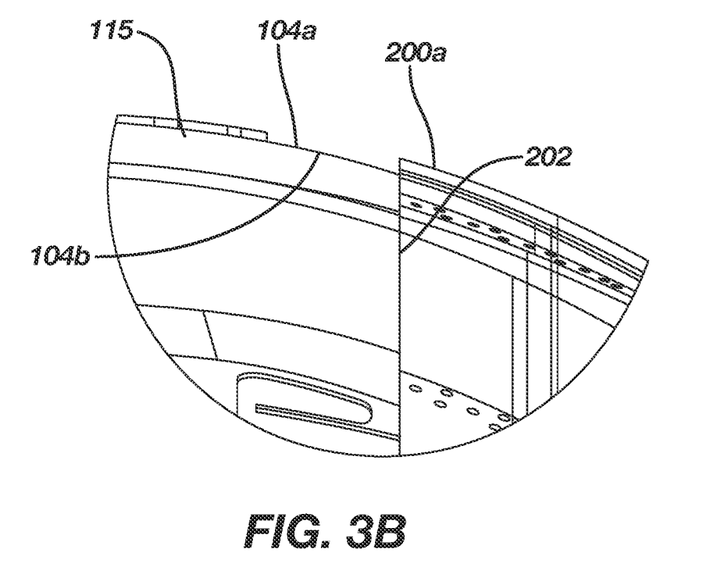
FIG. 3B is a blown-up side view of a portion of the membrane of FIG. 3A.
Figure 4:
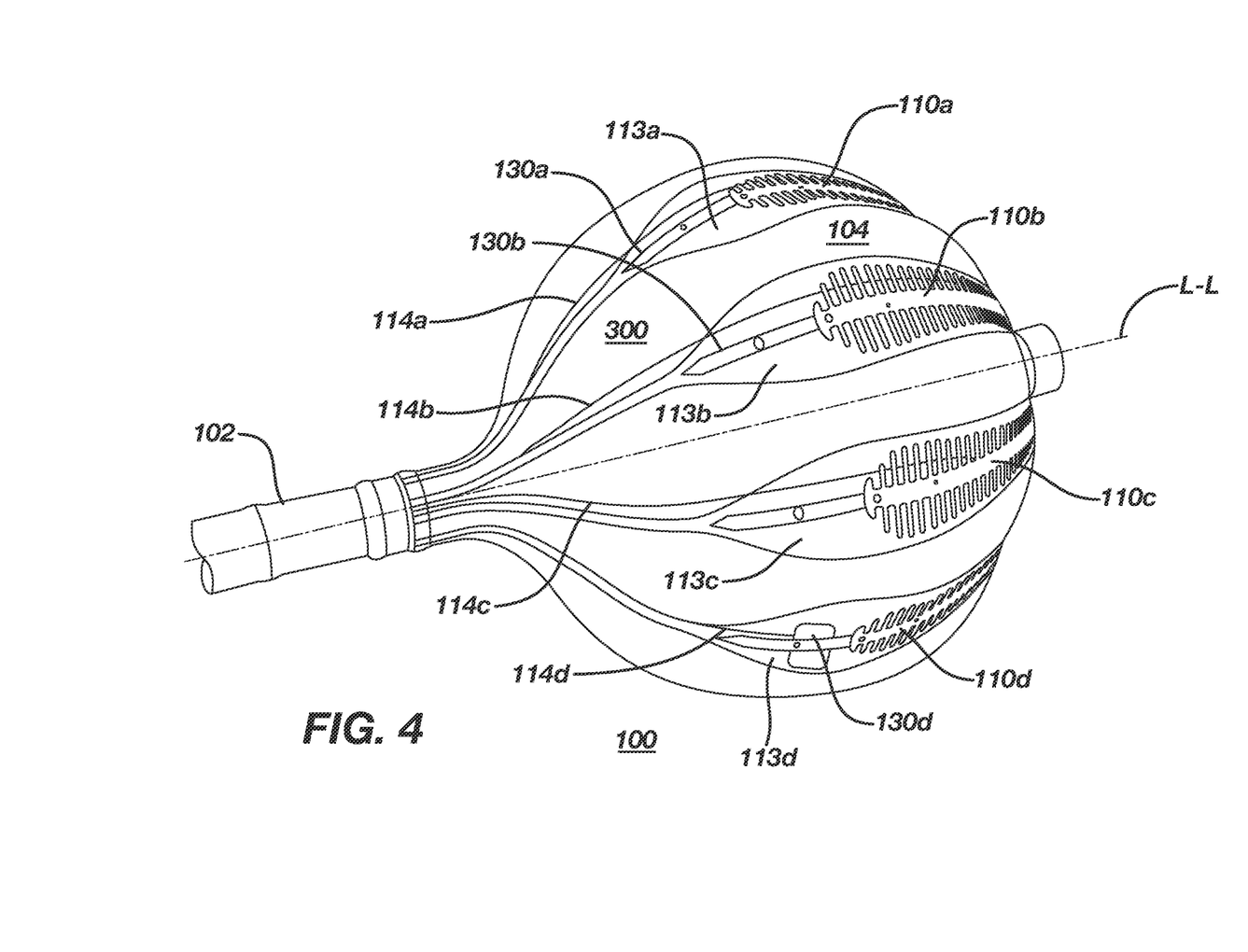
FIG. 4 is a color photograph of an actual prototype according to an embodiment described and illustrated herein.

As can be seen in FIG. 2, when group of wires 114a-114j are mounted on the membrane 104, each wire 114 is configured to extend from the tubular member 102 to the respective electrode 110 such that each wire follows the topographic outer surface 104a of membrane 104. In extending the wires 114 toward the tubular member 102, the wires 114 become exposed to the ambient environment (e.g., biological tissues or blood) as each wire 114 leaves the underside surface of each electrode or the underside surface of the substrate 113 (FIG. 3A). As each wire 114 may be used to conduct or transmit electrical energy or signals, it would be detrimental to expose the wires 114 to the ambient biological tissue environment. As such, we have devised a second expandable membrane 200 that encapsulates the one or more wires (114a-114j) between the second expandable membrane 200 and the first expandable membrane 104 so that the wires 114a-114j are constrained between the first and second expandable membrane (FIG. 4). Such configuration eliminates the exposure of the wires to the ambient environment yet still allowing the electrodes/thermocouples to be exposed to biological tissues so that the electrodes and thermocouples to work for their intended purposes. Moreover, as the wires 114 are constrained or captured between the first and second membranes, there is virtually no likelihood of the wires being entangled or mis-connected to the wrong electrode or thermocouple during assembly. In the preferred embodiment, each wire of the bifilar is coupled to a temperature sensor in the form of a thermocouple 116 disposed on or near each electrode 110.

It is noted that tubular member 102 defines a first internal passageway in the form of a lumen 102c, shown here as dashed lines in FIG. 3A, that extends from the first end 102a to the second end 102b of tubular member 102 so that the one or more wires are disposed in the first lumen 102c. To allow other instruments (e.g., guide wires, optical sensor etc.,) to be delivered through the balloon 104 (and outside of the distal-most portion 108 of balloon) the tubular member 102 can be provided with a second lumen 102d that extends through the membrane portions 106 and 108 to allow for another instrument to pass through the second lumen 102d. Additionally, the tubular member 102 can be provided with yet another internal passageway in the form of a third lumen 102e. Irrigation fluid can be provided in either of the second lumen 102d or third lumen 102e so that the irrigation fluid flows into the internal volume of the membrane 104, through openings or pores 120 provided through the membrane inner surface 104b and outer surface 104a to outside of the membrane 104 to the ambient environment (e.g., biological tissues or organ). Each electrode may have four irrigation openings formed on the electrode such that the electrode irrigation openings are aligned with the pores 120 of the membrane. In the preferred embodiment, lumen 102c, lumen 102d and 102e are configured or extruded as concentric passageways, in the form of a tube 102e within tube 102d within a tube 102c with outer tubular member 102. Tubular member 102 can be a suitable biocompatible polymer as is known to those skilled in the art.

Referring to FIG. 2, the plurality of electrodes 110a-110j extend from a substrate centroid 112 equiangularly about the longitudinal axis L-L from the first expandable distal membrane portion 108 towards the second expandable distal membrane portion 106 such that the second expandable membrane 200 encapsulates a portion of each of the electrodes (110a-110j) proximate the second expandable membrane portion 106. The second expandable membrane 200 has a border 202 (FIG. 1) that extends over a proximal portion (i.e., fish-head 115) of the electrode 110 outer surface (FIG. 2) while allowing the electrode fish-bone pattern 110 to be exposed to the ambient environment.

That is, each of the plurality of electrodes 110a-110j defines a fishbone pattern not covered by the second expandable membrane 200 to allow the fishbone electrodes to be exposed to the ambient environment. Each electrode (110a-110j) is coupled to the outer surface of the first expandable membrane 104 via a substrate 113 which itself is connected to or bonded to the outer surface 104a of the first expandable membrane 104. The electrode 110a-110j can have a portion of its perimeter bonded directly to membrane 104. A suitable seal 111 can be formed so that the seal 111 runs along the outer perimeter of the substrate 113 of each electrode (110a-110j). In a preferred embodiment, the seal 111 can be provided in the form of a polyurethane seal.

Referring to FIG. 3A, a radiopaque marker 130 is defined by a proximal fish-head portion of each electrode such that there can be respective radiopaque markers 130a, 130b, 130c, 130d, 130e, 130f, 130g, 130h, 130i and 130j for corresponding electrodes 110a-110j. To ensure that the location of each electrode can be determined while inside a body organ with x-rays, each electrode 110 may have a radiopaque marker (130a-130j) with each marker having a configuration different from other radiopaque markers on the other electrodes.

Referring to FIG. 1, a third expandable membrane 300 can be disposed proximate the first expandable distal membrane portion 108 so that the third expandable membrane 300 encircles an outer surface portion of the first expandable membrane 104 about the longitudinal axis L-L proximate the distal portion 108 of the membrane 104. The third expandable membrane encapsulates a portion of the substrate 113 (FIG. 3A) for each of the plurality of electrodes near distal portion 108 of membrane 104. Preferably, the third expandable membrane 300 allows for encapsulation of the substrates 113 of each electrode (110a-110j) as the substrates 113 converge to centroid 112 near the distal portion 108 of the membrane 104. A retaining ring 400 is disposed about the third expandable membrane 300 (near distal portion 108 of membrane 104) to hold the third expandable membrane 300 as well as the substrates 113 to the first expandable membrane 104. The third expandable membrane 300 can be bonded to the first expandable membrane 104 thereby capturing the substrate 113 therebetween the two membranes (104 and 300).

Figure 3C:
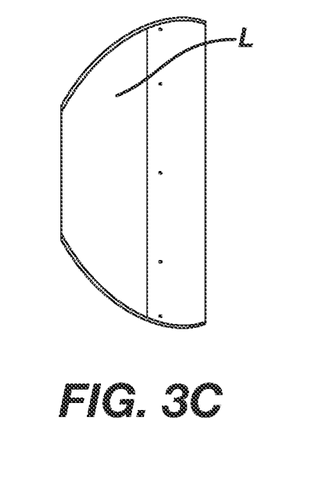
FIG. 3C illustrates a lateral or circumferential surface area (shaded portion) not covered by the hemispherical second and third expandable membranes of FIG. 1.

Referring to FIG. 3A, it is noted that the surface area of the membrane 104 that is exposed (i.e., not covered) by second expandable membrane 200a and third expandable membrane has a circumferential surface area L delineated between a virtual slice S1 (defined by the intersection of third expandable membrane 300 with first expandable membrane 104) orthogonal to axis L-L and virtual slice S2 orthogonal to the longitudinal axis L-L whereby slice S2 is defined by the intersection of the second expandable membrane 200 to the first expandable membrane 104. For clarity, it can be seen in FIG. 3C that if the first expandable membrane 104 approximates a sphere (when membrane 104 is expanded to its service characteristic) then the circumferential surface area L can be determined once the parameters of the spheroid body is known. In the preferred embodiment, shown in FIG. 4, the first expandable membrane 104 includes a circumferential surface area L (FIGS. 3A and 3C) of approximately 52% of a total surface area of the first expandable membrane 104. That is, the circumferential surface area L is the exposed surface area (without any electrode or substrate) of first expandable membrane 104 or outer circumferential area of first expandable membrane 104 that is also not covered by the second expandable membrane 200a and third expandable membrane 300. Further, it is noted that each substrate 113 for each electrode 110 includes a substrate surface area approximately 8% of the exposed outer circumferential surface area L of the first expandable membrane 104. In the preferred embodiments, the second expandable membrane 200, 200a and third expandable membrane 300 cover approximately half of the outer surface area of the first expandable membrane 104.

In the preferred embodiments, the first expandable membrane includes a generally spheroidal member with a diameter as referenced to the longitudinal axis L-L of about 30 millimeters and the second expandable membrane and the third expandable membrane each includes a hemi-spherical member with the respective major diameter of each hemi-spherical member being less than 30 mm. In the preferred embodiments, the total surface area of membrane 104 is about 4500 squared-mm while the circumferential surface area L is about 2400 squared-mm and each flexible substrate 113 is about 200 squared-mm when the membrane 104 is at its fully expanded (i.e., designed) configuration, shown exemplarily in FIG. 4.

The balloon 104 of the diagnostic/therapeutic catheter has an exterior wall or membrane 104a of a bio-compatible material, for example, formed from a plastic such as polyethylene terephthalate (PET), polyurethane or PEBAX®. The tubular shaft 102 and the distal shaft end 102a define a longitudinal axis L-L of the balloon 104. The balloon 104 is deployed, in a collapsed configuration as described in commonly-owned U.S. patent application Ser. No. 15/939,154 filed on Mar. 28, 2018 (via the lumen 23 of the probe 20 in this prior application, which is incorporated by reference herein to this present application). The membrane 104a of the balloon 104 is formed with irrigation pores or apertures 120 (shown in FIG. 3A) through which the fluid (e.g., saline) can exit from the interior of the balloon 104 to outside the balloon for cooling the tissue ablation site at the ostium.

As described earlier in relation to FIG. 2, membrane 24 supports and carries a combined electrode and temperature sensing member which is constructed as a multi-layer flexible circuit electrode assembly 110a-110j. The "flex circuit electrode assembly" 110a-110j may have many different geometric configurations than as shown here. In the illustrated embodiment, the flex circuit electrode assembly 110a-110j has a plurality of radiating substrates or strips 113a-113j, as best seen in FIG. 1. The substrates 113a-113j are evenly distributed about the distal end 108 and the balloon 104. Each substrate 113a-113j has wider proximal portion that gradually tapers to a narrower distal portion as referenced to the longitudinal axis.

For simplicity, the flex circuit electrode assembly 110 is described with respect to one of its substrate 113 as shown in FIG. 3A, although it is understood that following description may apply to each substrate 113 of the assembly 110. The flex circuit electrode assembly 110 includes a flexible and resilient sheet substrate material 113, constructed of suitable bio-compatible materials, for example, polyimide. In some embodiments, the sheet substrate material 113 has a greater heat resistance (or a higher melting temperature) compared to that of the balloon membrane 104. In some embodiments, the substrate material 113 is constructed of a thermoset material having a decomposition temperature that is higher than the melting temperature of the balloon membrane 104 by approximately 100 degrees Celsius or more.

The substrate material 113 is formed with one or more irrigation pores or apertures (not labeled) that are in alignment with the irrigation apertures 120 of the balloon member 104 so that fluid passing through the irrigation apertures 120 and (not labeled) can pass to the ablation site on the ostium.

The substrate material 113 has a first or outer surface facing away from the balloon membrane 104, and a second or inner surface facing the balloon membrane 104. On its outer surface, the substrate material 113 supports and carries the contact electrodes 110. The configuration or trace of the contact electrode 110 may resemble a "fishbone" but it should be noted that the invention is not limited to such configuration. In contrast to an area or "patch" ablation electrode, the fingers of the contact electrode 110 advantageously increase the circumferential or equatorial contact surface of the contact electrode 110 with the ostium while void regions between adjacent fingers advantageously allow the balloon 104 to collapse inwardly or expand radially as needed at locations along its equator. In the illustrated embodiment, the fingers have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 113. In the illustrated embodiment, there are 22 fingers extending across (past each lateral side of) the elongated portion. In some embodiments, the contact electrode 110 includes gold with a seed layer between the gold and the membrane 104. The seed layer may include titanium, tungsten, palladium, silver, or combinations thereof.

Figure 5:
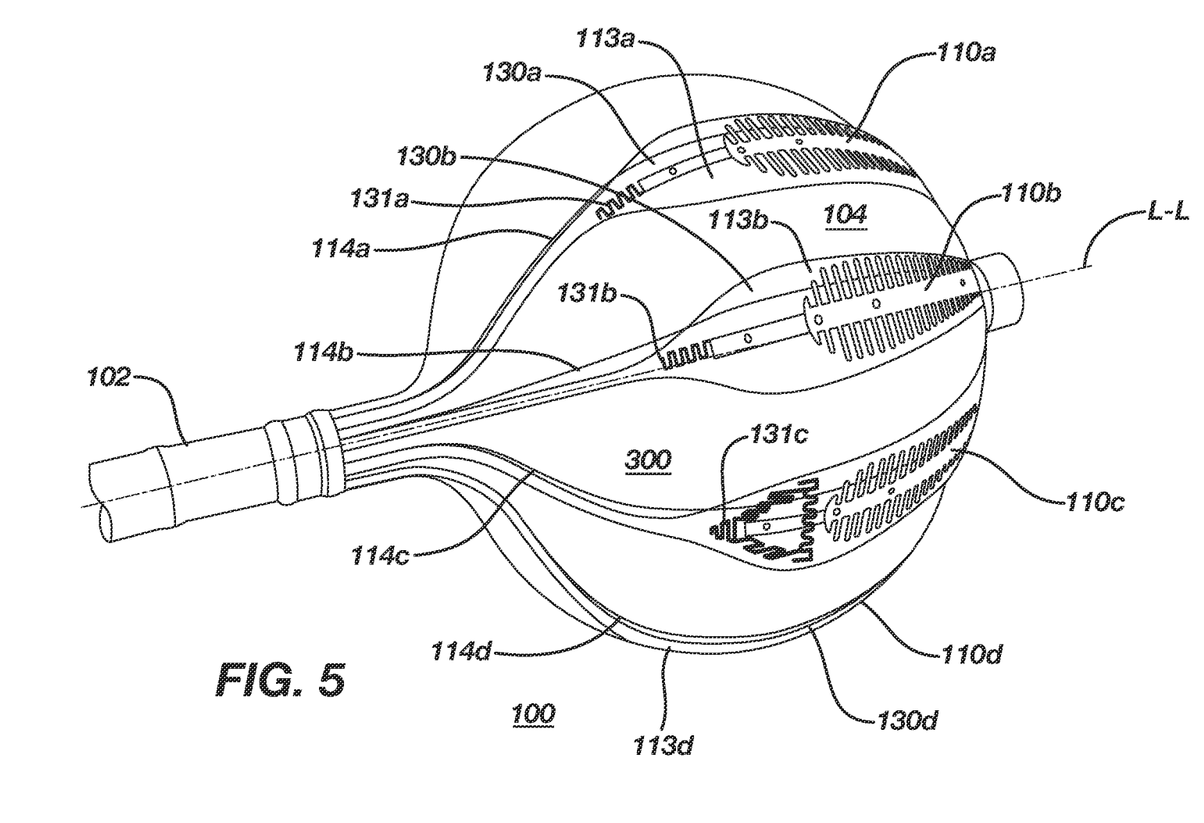
FIG. 5 is a color photograph of yet another prototype of the embodiments described and illustrated herein.

As shown in FIG. 5, the flexible electrode may have its radiopaque marker in the variation identified as 131a, 131b, 131c and so on to assist in the identification of the electrode being energized. The markers 131a-131j have various serpentine configurations (as compared to FIG. 4) to allow for increased flexibility due to the presence of the second membrane 200 which tend to reduce the flexibility of the device near the markers 131a-131j.

Description of the diagnostic/therapeutic catheter in accordance with the foregoing disclosure may be found in U.S. patent application Ser. No. 15/360,966, published as U.S. Patent Application Publication No. 2017/0312022, which is incorporated by reference herein in its entirety and attached hereto this application in the Appendix.

Any of the examples or embodiments described herein may include various other features in addition to or in lieu of those described above. The teachings, expressions, embodiments, examples, etc. described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but, in any order, if the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. An electrophysiology probe comprising:
   a tubular member extending along a longitudinal axis from a first end to a second end;
   a first expandable membrane having an outer surface and an inner surface disposed about the longitudinal axis, the first expandable membrane having a first expandable membrane portion being coupled to the second end of the tubular member and a second expandable membrane portion spaced apart from the first expandable membrane portion along the longitudinal axis, the first expandable membrane configured to be expanded from a compressed shape to a balloon shaped member;
   a plurality of electrodes disposed on the outer surface of the first expandable membrane;
   one or more wires connected to each of the plurality of electrodes, each of the one or more wires extending from the tubular member to a respective electrode of the plurality of electrodes;
   a second expandable membrane that encapsulates the one or more wires between the second expandable membrane and the first expandable membrane so that the one or more wires are constrained between the first and second expandable membranes with the plurality of electrodes exposed to an external ambient environment; and a third expandable membrane disposed proximate the first expandable membrane portion so that the third expandable membrane encircles a portion of the first expandable membrane about the longitudinal axis, wherein the third expandable membrane encapsulates a portion of a substrate for each of the plurality of electrodes between the first expandable membrane and the third expandable membrane, and wherein the third expandable membrane is spaced apart from the second expandable membrane along the longitudinal axis.

2. The electrophysiology probe of claim 1, wherein the tubular member defines a first lumen that extend extends from the first end to the second end so that the one or more wires are contained in the first lumen.

3. The electrophysiology probe of claim 1, wherein the tubular member defines a second lumen that extends through the first expandable membrane to allow for another instrument to pass through the second lumen.

4. The electrophysiology probe of claim 1, wherein the tubular member defines a third lumen that extends to a portion within the first expandable membrane, the third lumen configured to allow irrigation fluid to be delivered to the portion within the first expandable membrane.

5. The electrophysiology probe of claim 1, wherein the first expandable membrane includes a plurality of openings that extends through the first expandable membrane to allow for irrigation fluid to flow from inside the first expandable membrane to outside of the first expandable membrane.

6. The electrophysiology probe of claim 1, wherein the plurality of electrodes extend from a central electrode portion equiangularly about the longitudinal axis from the first expandable membrane portion towards the second expandable membrane portion such that the second expandable membrane encapsulates a portion of each of the plurality of electrodes proximate the second expandable membrane portion.

7. The electrophysiology probe of claim 1, wherein each of the plurality of electrodes defines a fishbone pattern not covered by the second expandable membrane.

8. The electrophysiology probe of claim 1, wherein each of the plurality of electrodes is coupled to the outer surface of the first expandable membrane via the substrate.

9. The electrophysiology probe of claim 1, wherein a radiopaque marker is defined by a fish-head portion of each of the plurality of electrodes.

10. The electrophysiology probe of claim 1, wherein each of the plurality of electrodes includes a radiopaque marker having a configuration different from other radiopaque markers on others of the plurality of electrodes.

11. The electrophysiology probe of claim 1, further comprising a retaining ring disposed about the third expandable membrane.

12. The electrophysiology probe of claim 1, wherein the first expandable membrane includes a circumferential surface area of approximately 52% of a total surface area of the first expandable membrane that is not covered by the second and third expandable membranes.

13. The electrophysiology probe of claim 1, wherein the substrate for each of the plurality of electrodes includes a substrate surface area approximately 8% of an outer circumferential surface area of the first expandable membrane.

14. The electrophysiology probe of claim 1, wherein the plurality of electrodes comprises ten electrodes disposed equiangularly about the longitudinal axis on the first expandable membrane.

15. The electrophysiology probe of claim 1, wherein the second expandable membrane and the third expandable membrane cover approximately half of the outer surface area of the first expandable membrane.

16. The electrophysiology probe of claim 1, wherein the first expandable membrane includes a generally spheroidal member with a diameter as referenced to the longitudinal axis of about 30 millimeters and wherein the second expandable membrane and the third expandable membrane each includes a hemi-spherical member.

17. The electrophysiology probe of claim 1, wherein the first expandable membrane includes a first configuration disposed in a tubular member of less than 8 French and a second configuration disposed outside the tubular member of about 30 millimeters as referenced to the longitudinal axis.

* * * * *